United States Patent [19]

Ohki et al.

[11] Patent Number: 5,043,422

[45] Date of Patent: Aug. 27, 1991

[54] ANTI-HIV PEPTIDE AND MODIFIED ANTI-HIV PEPTIDE

[76] Inventors: Kohji Ohki, Ra Bahn No. 101, 9-chome, Shinkawa 4-jo, Kita-ku, Sapporo-shi, Hokkaido; Kazuyoshi Ikuta, 2-3, Nishi 9-chome, Minami 16-jo, Chuo-ku, Sapporo-shi, Hokkaido; Kazutaka Ohmura, 3-3-14, Kitakashiwa, Kashiwa-shi, Chiba-ken; Shiro Kato, 4-23-7, Fujishirodai, Suita-shi, Osaka-fu, all of Japan

[21] Appl. No.: 547,809

[22] Filed: Jul. 2, 1990

[30] Foreign Application Priority Data

Jul. 5, 1989 [JP] Japan .................................. 1-172053

[51] Int. Cl.$^5$ ........................ A61K 37/02; C07K 7/10
[52] U.S. Cl. .................................................... 530/324
[58] Field of Search ............................ 530/324; 514/12

[56] References Cited

U.S. PATENT DOCUMENTS

| 4,812,556 | 3/1989 | Vahlne et al. | 530/324 |
| 4,868,287 | 9/1989 | Sikes et al. | 530/324 |
| 4,956,273 | 9/1990 | Kennedy et al. | 530/324 |
| 4,957,737 | 9/1990 | Heimer et al. | 530/324 |
| 4,983,387 | 1/1991 | Goldstein et al. | 530/324 |

OTHER PUBLICATIONS

The Journal of Immunology, "Binding of the Human Retrovirus HTLV-III/LAV/ARV/HIV to the CD(T) Molecule", McDougal et al., vol. 137, pp. 2937–2944, 11/86.

Science, "Synthetic CD Peptide Derivatives that Inhibit HIV Infection and Cytopathicity", pp. 712–716, 8/88, Lifson et al.

Primary Examiner—Lester L. Lee
Attorney, Agent, or Firm—Malcolm B. Wittenberg

[57] ABSTRACT

A peptide having anti-HIV activity consists of an amino acid chain represented by Asn-Phe-Pro-Leu-Ile-Ile-Lys-Asn-Leu-Lys-Ile-Glu-Asp-Ser-Asp-Thr-Tyr-Ile-Cys-Glu-Val-Glu-Asp-Gln-Lys-Glu. The Cys underlined in the above amino acid chain may be replaced by Phe, Ser, Cys$^{Acm}$ or Cys$^{Bzl}$.

5 Claims, No Drawings

ANTI-HIV PEPTIDE AND MODIFIED ANTI-HIV PEPTIDE

BACKGROUND OF THE INVENTION

This invention relates to an anti-HIV (human immunodeficiency virus) peptide and a modified anti-HIV peptide.

The anti-HIV peptide of the present invention functions to inhibit infection of HIV (human immunodeficiency virus) and may be applied to treatment or prevention of manifestation of acquired human immunodeficiency syndromes (AIDS).

As a drug or medicament for treatment or prevention of manifestation of AIDS by HIV, inhibitors for reverse transcriptase owned intrinsically by HIV and necessitated for replication of the virus particles, are practically used. However, these inhibitors are not desirable because of the powerful toxicity thereof against the normal cells. Although proper vaccination may be thought of as a measure against the manifestation of the disease, difficulties are met in the evolution of a proper vaccine because the antigenicity of the protein covering the outer surface of the HIV may be changed easily by mutation and no reports have been made on the examples of success in the evolution of suitable vaccines.

Thus, the evolution of drugs or medicaments which are more powerful and lower in toxicity is progessing briskly. For example, various medicaments have been proposed for preventing the infection by inhibiting the binding of HIV to the cells.

A first one of such medicaments is an antibody capable of being bound to gp 120 or gp 41 which is the protein covering the outer surface of HIV. Such antibody may be prepared in the form of an antiserum or as a monoclonal antibody by inoculating a suitable animal with the protein. However, since the antigenicity of the above mentioned protein is not necessarily constant, it is necessary to find an antibody against the amino acid sequence which is not subject to variation. Moreover, since the usually available antibody is derived from animals, the antibody itself exhibits immunogenicity with respect to a human so that the antibody cannot be used repeatedly.

In the second place, it has been attempted to administer an antibody against the CD4 molecule, which is the HIV receptor on the cell, to thereby sheath the cell for exempting the cell from infection by HIV. Although the HIV may be prevented from being bound to the cell, the function of the normal cells is affected simultaneously.

In the third place, it has been attempted to apply the CD4 molecule itself, which is the HIV receptor, to the treatment for obviating the problem in employing the antibody. It is generally recognized that the CD4 molecule, which is soluble, is effective to prevent propagation of infection by binding the gp 120 of HIV, while not interfering with the function of normal cells, such as that of macrophages, or the class II specific interaction among the T cells. This soluble CD4 molecule has already been prepared by application of a genetic engineering technique (Hussey, R.E. et al., Nature, 331, 78, 1988).

However, the soluble CD4 molecule, when used actually as the anti-HIV drug, presents problems in connection with the shortness of the time period during which the efficacy of the drug in the blood is reduced to half, non-sustained efficacy and larger dosage. Thus, it has been felt necessary to improve the soluble CD4 molecule (Capon, D.J. et al., Nature, 337, 525–531, 1989).

In the fourth place, a method has been proposed which takes advantage of a region of the peptide of the CD4 molecule capable of being specifically bound with the gp 120 of HIV. This peptide is comprised only of a portion taking part in binding with gp 120 and may be bound with gp 120 in the same manner as is the soluble CD4 molecule so that the peptide is highly unlikely to be involved in any other unnecessary reactions and hence exhibits high specificity. Also, this peptide may be prepared easily as drugs in various ways, since it is prepared by chemical synthetic methods. As such chemically synthesized peptide, a peptide having 63 amino acid residues has been proposed, as in Hayashi, Y. et al., Archives of Virology, 105, 129–135, 1989. This peptide, however, is inconvenient since it cannot be mass-produced without difficulties by the peptide synthesis technique because of its longer amino acid chain length. Another peptide having 19 amino acid residues has also been proposed by Lisfson, J.D. et al., Science, 241, 712–716, 1988. Although shorter in amino acid chain length, this peptide is not satisfactory in anti-HIV activity. Thus, there is a strong demand for a peptide which has a shorter amino acid chain length and yet is superior in anti-HIV activity.

SUMMARY OF THE INVENTION

An object of this invention is to provide a shorter amino acid chain section of the amino acid chain of the CD4 molecule capable of inhibiting infection or propagation of HIV, that is an anti-HIV peptide and a modified anti-HIV peptide.

In accordance with the present invention, there is provided a peptide having anti-HIV activity, the peptide consisting of an amino acid chain represented by Asn-Phe-Pro-Leu-Ile-Ile-Lys-Asn-Leu-Lys-Ile-Glu-Asp-Ser-Asp-Thr-Tyr-Ile-Cys-Glu-Val-Glu-Asp-Gln-Lys-Glu-Glu.

In accordance with the present invention, there is also provided a peptide having anti-HIV activity, the peptide consisting of an amino acid chain represented by Asn-Phe-Pro-Leu-Ile-Ile-Lys-Asn-Leu-Lys-Ile-Glu-Asp-Ser-Asp-Thr-Tyr-Ile-Phe-Glu-Val-Glu-Asp-Gln-Lys-Glu-Glu.

In accordance with the present invention, there is also provided a peptide having anti-HIV activity, the peptide consisting of an amino acid chain represented by Asn-Phe-Pro-Leu-Ile-Ile-Lys-Asn-Leu-Lys-Ile-Glu-Asp-Ser-Asp-Thr-Tyr-Ile-Ser-Glu-Val-Glu-Asp-Gln-Lys-Glu-Glu.

In accordance with the present invention, there is also provided a modified peptide having anti-HIV activity, the peptide consisting of an amino acid chain represented by Asn-Phe-Pro-Leu-Ile-Ile-Lys-Asn-Leu-Lys-Ile-Glu-Asp-Ser-Asp-Thr-Tyr-Ile-CysAcm-Glu-Val-Glu-Asp-Gln-Lys-Glu-Glu wherein Acm represents an acetoamidomethyl group.

In accordance with the present invention, there is also provided a modified peptide having anti-HIV activity, the peptide consisting of an amino acid chain represented by Asn-Phe-Pro-Leu-Ile-Ile-Lys-Asn-Leu-Lys-Ile-Glu-
Asp-Ser-Asp-Thr-Tyr-Ile-Cys$^{Bzl}$-Glu-Val-Glu-
Asp-Gln-Lys-Glu-Glu wherein Bzl represents a benzyl group.

PREFERRED EMBODIMENTS OF THE INVENTION

The present invention is explained in more detail hereinbelow.

The present inventors have prepared, on the basis of the amino acid sequence determined by the DNA base sequence coding the CD4 molecule (Maddon, P.J.et. al., Cell, 47, 333 to 348, 1986), various partial peptides of the CD4 molecule and added the partial peptides to an HIV receptive cell strain MT-4 and to the HIV infected system to investigate into the anti-HIV activity, that is the activity inhibiting cell extinction or denaturation caused by HIV infection. As a result thereof, the present inventors have found that the following partial peptides represented by the sequences (1) to (5) below, which are the partial peptide covering 68th to 94th amino acids as counted from the N-terminal end and partial peptides obtained by partially modifying or changing the firstly mentioned partial peptides, exhibit a highly superior anti-HIV activity. Incidentally, each amino acid residue is shown by three letter abbreviation.

(1) Asn-Phe-Pro-Leu-Ile-Ile-Lys-Asn-Leu-Lys-Ile-Glu-Asp-Ser-Asp-Thr-Tyr-Ile-Cys-Glu-Val-Glu-Asp-Gln-Lys-Glu-Glu.

(2) Asn-Phe-Pro-Leu-Ile-Ile-Lys-Asn-Leu-Lys-Ile-Glu-Asp-Ser-Asp-Thr-Tyr-Ile-Phe-Glu-Val-Glu-Asp-Gln-Lys-Glu-Glu.

(3) Asn-Phe-Pro-Leu-Ile-Ile-Lys-Asn-Leu-Lys-Ile-Glu-Asp-Ser-Asp-Thr-Tyr-Ile-Ser-Glu-Val-Glu-Asp-Gln-Lys-Glu-Glu.

(4) Asn-Phe-Pro-Leu-Ile-Ile-Lys-Asn-Leu-Lys-Ile-Glu-Asp-Ser-Asp-Thr-Tyr-Ile-Cys$^{Acm}$-Glu-Val-Glu-Asp-Gln-Lys-Glu-Glu (Acm: acetoamidomethyl group).

(5) Asn-Phe-Pro-Leu-Ile-Ile-Lys-Asn-Leu-Lys-Ile-Glu-Asp-Ser-Asp-Thr-Tyr-Ile-Cys$^{Bzl}$-Glu-Val-Glu-Asp-Gln-Lys-Glu-Glu (Bzl:benzyl group)

In accordance with the present invention, the anti-HIV peptide or the modified anti-HIV peptides (1) to (5) above may be prepared by, for example, a first method, i.e. a solid-phase method employing an Fmoc amino acid (Sheppard, R.C. et. al., J. Chem. Soc., Chem. Comm., 165–166, 1985). Specifically, an Fmoc amino acid ester of pentafluorophenyl Pfp), corresponding to the C-terminal end of the peptide represented by any of the sequences (1) to (5) above, is bound to a high molecular carrier or substrate of, for example, p-alkoxybenzyl alcohol resin, in , for example, dimethylformamide, in the presence of 4-dimethylaminopyridine. Then, another Fmoc amino acid easter of Pfp to be bound next is then bound by condensation reaction to both the high molecular carrier and to the previously bound Fmoc amino acid Pfp ester. By the similar sequence of operations, the corresponding Fmoc amino acid Pfp esters are formed on the high molecular carrier. It is noted that threonine (Thr) and serine (Ser) are preferably introduced with the use of 1-oxo-2-hydroxy-dihydro-benzotriazine (DHBT) ester. After termination of the coupling reaction of each amino acid, the high polymer carrier having the peptide bound thereto is treated with a 20 wt.% solution of piperidine in dimethylformamide for eliminating the Fmoc groups at the N-terminal ends. It is then acted upon by, for example, TFA-tioanisole at room temperature in the presence of n-cresole for eliminating the whole protective groups, while at the same time the desired partial peptides are recovered from the high polymer carrier and purified as an ultimate product.

The second method for synthesizing the anti-HIV peptide and the modified anti-HIV peptide of the present invention is a solid phase method employing the Boc-amino acid according to Merrifield, J.Am. Chem. Soc., 85, 2149 (1963). In this second method, when an amino acid side chain is modified as represented by the chains (4) and (5) above, a stable modified amino acid is introduced into the peptide under the condition of eliminating the protective groups.

Besides the above mentioned methods of producing the partial peptides and modified partial peptides, the peptides may also be produced by other conventional chemical synthetic methods, methods of producing a DNA corresponding to the desired peptide and introducing the DNA into a suitable vector for production in animal cells or microorganisms to produce the desired partial peptide, or methods of chemically modifying the produced peptide in a suitable manner.

The anti-HIV peptide or modified anti-HIV peptide according to the present invention may be produced more advantageously because the length of the amino acid chain thereof is less than half that of the conventional peptide as proposed in Hayashi, Y. et. al., Archives of Virology, 105, 129–135, 1989, and hence the time and labor involved in the synthesis may be reduced to one fourth or less. With the amino acid chain length thus reduced, the antigenicity or toxicity such as inhibition of the function of the in vivo CD4 molecule may be suppressed to a minimum, while the excellent anti-HIV activity is demonstrated. On the other hand, the anti-HIV effect may also be augmented by modifying the side chain of a suitable amino acid residue or by replacing a specific amino acid residue by another amino acid.

EXAMPLES OF THE INVENTION

The present invention will be explained in more detail with reference to several Examples.

EXAMPLE 1

For synthesizing the peptide consisting of the following amino acid chain :

Asn-Phe-Pro-Leu-Ile-Ile-Lys-Asn-Leu-Lys-Ile-Glu-Asp-Ser-Asp-Thr-Tyr-Ile-Cys$^{Acm}$-Glu-Val-Glu-Asp-Gln-Lys-Glu-Glu (Acm: acetoamidomethyl group), the glutamic acid at the C terminal end of the peptide was introduced by the ester linkage on a p-alkoxy benzyl alcohol Resin (0.2 mmol) (0.35 meq OH/g, Polystyrene 1% Divinyl benzene Copolymer, manufactured by Kokusan Chemical Works, Ltd.) in dimethylformamide (DMF), using 1 mmol of its derivative Fmoc-Glu(Acm)-OPfp active ester and 0.2 mmol of DMAP (4-dimethyl aminopyridine) as a catalyst.

The protective groups for the side chains of the Fmoc-amino acid derivatives (manufactured by Milligen Division of Millipore Ltd.) were Asp($OB_ut$), Glu($OBu^t$), Thr($Bu^t$), Ser($Bu^t$), Tyr($Bu^t$), Lys(Boc), His(Boc), Arg(Mtr) and Cys(Acn). Each condensation reaction for production of the peptide chain was performed, with the exception of that for threonine and serine, with the use of 2.5 eq. of Pfp(pentafluorophenyl) active ester in DMF in the presence of 0.2 mmol of HOBT(1-hydroxybenzotriazole). On the other hand, threonine and serine were introduced using DHBT(3, 4-dihydro-3-hydroxy-4-oxo-1, 2, 3-benzotriazine)ester.

Each Fmoc group was removed by using a 20 wt.% piperidine solution in dimethylformamide, while each coupling reaction was monitored with ninhydrine.

After the termination of all of the coupling reactions, the Fmoc groups remaining at the N-terminal end was eliminated with a 20 wt.% of piperidine in DMF to set the $NH_2$-group free. Then, for eliminating all of the protective groups and separating the peptide from the resin, the resin with the peptide affixed thereto was treated with TFA-thioanisole for three hours at room temperature in the presence of m-cresole and filtered through a glass filter to remove the resin. The filtrate was condensed at room temperature and ether was added thereto to produce powders, which were then recovered and dissolved in a formic acid ammonium buffer so as to be then eluted in 0.5N AcOH by "Sephadex G-25" (manufactured by Pharmacia). The eluted product was then desalted and purified so as to be then purified by HPLC.

For fractionation by HPLC, the eluted product was caused to flow at a flow velocity of 1 ml per minute through a column of "Nucleosil 100 5c18" (4.0×150 mm)column at a concentration gradient of 10 to 60 % of acetonitrile in 0.1 wt.% TFA and monitored at 210 and 260 nm. The objective anti-HIV peptide of the present invention (partial peptide 68 to 94) was eluted at a holding time of 16.8 minutes. A portion of the produced fraction was analysed by using "835S amino assist analyzer" manufactured by Hitachi Seisakusho KK and identified as the objective partial peptide.

EXAMPLE 2

For preparing a peptide consisting of the following amino acid chain :

Asn-Phe-Pro-Leu-Ile-Ile-Lys-Asn-Leu-Lys-Ile-Glu-Asp-Ser-Asp-Thr-Tyr-Ile-Cys$^{Bzl}$-Glu-Val-Glu-Asp-Gln-Lys-Glu-Glu (Bzl:benzyl group), 0.05 mmol scal. of Boc - Glu(OBzl) -Pam resin, manufactured by Applied Biosystems Inc., was used as the starting material of glutamic acid which is the C-terminal end of the peptide. The peptide chain was subjected to sequential extension, using an automatic peptide synthesizer "model 430A" manufactured by Applied Biosystem Inc. (Program version 1.40). Side chain protection of the Boc amino acid derivative employed in the peptide chain extension (manufactured by Peptide Laboratories) was by Asp(cHex), Cys(Bzl), Glu(cHex), Lys(ClZ), Ser(Bzl), Thr(Bzl), Thr(Bzl) and Tyr(BrZ). Each condensation reaction for extending the peptide chain was performed in DMF by synthesizing 2.0 eq. of acid anhydrides of Boc-amino acids corresponding to the sequence in a $CH_2Cl_2$(dichloromethane)-DMF liquid mixture using DCC (dicyclohexycarbodiimide) except aspartic acid and glutamic acid. The condensation reaction for aspartic acid and glutamic acid was performed by using an HOBt(1-hydroxybenzotriazole)ester for each of Boc-Asn and Boc-Gln.

Each Boc group was removed by using a 50 wt.% TFA (trifluoroacetic acid) solution in $CH_2Cl_2$.

After the termination of all of the amino acid condensation reactions, the Boc group at the N-terminal end as well as the whole protective groups were removed by treatment in a 10 wt.% anisole/anhydrous HF (hydrogen fluoride) under ice cooling at −5° C. for 30 minutes. Simultaneously, the peptide was separated from the resin and HF was distilled off in vacuum. The residues were washed with ether and the peptide was dissolved in TFA. After the resin was removed by a glass filter, the filtrate was concentrated in vacuum and dried ether was added to the residues to produce powders.

The produced powders, which were the crude peptide product, were purified by reversed phase HPLC for fractionation in the same way as in Example 2.

EXAMPLES 3 to 5

The peptides consisting of the following amino acid chains were synthesized in the same way as in Example 1.

Asn-Phe-Pro-Leu-Ile-Ile-Lys-Asn-Leu-Lys-Ile-Glu-Asp-Ser-Asp-Thr-Tyr-Ile-Cys-Glu-Val-Glu-Asp-Gln-Lys-Glu-Glu.(Example 3)

Asn-Phe-Pro-Leu-Ile-Ile-Lys-Asn-Leu-Lys-Ile-Glu-Asp-Ser-Asp-Thr-Tyr-Ile-Phe-Glu-Val-Glu-Asp-Gln-Lys-Glu-Glu.(Example 4)

Asn-Phe-Pro-Leu-Ile-Ile-Lys-Asn-Leu-Lys-Ile-Glu-Asp-Ser-Asp-Thr-Tyr-Ile-Ser-Glu-Val-Glu-Asp-Gln-Lys-Glu-Glu.(Example 5)

EXAMPLE 6

A cultured solution of the MOLT-4 cells, which were already sustainedly infected by HIV-1(HTLV-IIIB), was used as the HIV solution and diluted in ten stages. Into these diluted cultured solutions was introduced at a rate of 1 mg/ml. each of the peptide produced in Example 3 and, as controls, a peptide consisting of 74th to 94th amino acids (abbreviated to control 74-94), a peptide consisting of 86th to 104th amino acids (abbreviated to control 86-104), a peptide consisting of 86th to 107th amino acids (abbreviated to control 86-107) and a peptide consisting of 105th to 120th amino acids (abbreviated to control 105-120), which were synthesized in the same method as described in Example 1. Mixtures of the diluted cultured solutions and these peptides were maintained at room temperature for 30 minutes. These mixtures each were mixed with HIV-sensitive MT - 4 cell at a rate of $1 \times 10^6$ cells/ml and a vol/vol mixture ratio of 1 : 1 so that the total volume was 0.2 ml. Each of the resulting mixtures was introduced into an RPMI - 1640-10% FCS culture liquid and maintained in a carbonic gas incubator at 37° C. for four days. For measuring the anti-HIV activity of each partial peptide, the infectious index or HIV-1 titer was measured by an immunofluorescent method employing a monoclonal antibody against the gag protein p18 of HIV, and the HIV activity inhibit rate, that is the rate of lowering the HIV-1 titer by the above mentioned partial peptide containing diluted HIV solutions, with the partial peptide acting as the inhibitor, was measured in accordance with the following formula :

100−(HIV-1 titer of inhibitor/
HIV-1 titer of control)×100

The results are shown in Table 1.

TABLE 1

| Partial Peptides in Inhibitor | HIV-1 Titer | Inhibit Rate (%) |
|---|---|---|
| (control) | $10^{3.5}$ | 0 |
| 68-94(Ex. 3) | $10^{1.5}$ | 99 |
| 74-94 | $10^{2.5}$ | 90 |
| 74-104 | $10^{2.5}$ | 90 |
| 86-104 | $10^{2.5}$ | 90 |
| 86-107 | $10^{2.5}$ | 90 |
| 105-120 | $10^{3.5}$ | 0 |

It is noted that the HIV-1 titer represents the limit dilution ratio at which the diluted virus solution demonstrates the infectious potential. Thus, the higher the infectious potential, the higher becomes the infectious index. In other words, stronger anti-HIV activity is demonstrated when the infection is not caused with a virus solution thicker in concentration than the control. In the above table, the control is the virus solution which is free from various partial peptides acting as the above mentioned inhibitor.

It is seen from Table 1 that the anti-HIV higher than the inhibit rate of 99% was noticed with the partial peptide prepared in Example 3, that is the peptide consisting of the 68th to 94th amino acids counted from the N-terminal end of the CD4 molecule, and that only weak anti-HIV activity was noticed with the partial peptides further away from the N-terminal end than the partial peptide of Example 3.

EXAMPLE 7

The HIV-titers were measured in the same way as in Example 6 except that the partial peptides prepared in Examples 1 to 5 were used as the partial peptides constituting the inhibitors, and that the HIV-1 titer of the control was set to $10^{6.5}$, to find the inhibit rates. The results are shown in Table 2.

TABLE 2

| Partial peptides in Inhibitor | HIV-1 Titer | Inhibit Rates (%) |
|---|---|---|
| (control) | $10^{6.5}$ | 0 |
| Peptide of Ex. 3 | $10^{3.5}$ | 99.9 |
| Peptide of Ex. 1 | $10^{3.5}$ | 99.9 |
| Peptide of Ex. 2 | $10^{1.5}$ | 99.999 |
| Peptide of Ex. 4 | $10^{3.5}$ | 99.9 |
| Peptide of Ex. 5 | $10^{4.5}$ | 99 |

It is seen from the results of Table 2 that both the anti-HIV peptides and the modified anti-HIV peptides of the present invention exhibit superior inhibitive effects with respect to the HIV activity.

Although the present invention has been described with reference to the specific examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A peptide having anti-HIV activity, said peptide consisting of an amino acid chain represented by Asn-Phe-Pro-Leu-Ile-Ile-Lys-Asn-Leu-Lys-Ile-Glu-Asp-Ser-Asp-Thr-Tyr-Ile-Cys-Glu-Val-Glu-Asp-Gln-Lys-Glu-Glu.

2. A peptide having anti-HIV activity, said peptide consisting of an amino acid chain represented by Asn-Phe-Pro-Leu-Ile-Ile-Lys-Asn-Leu-Lys-Ile-Glu-Asp-Ser-Asp-Thr-Tyr-Ile-Phe-Glu-Val-Glu-Asp-Gln-Lys-Glu-Glu.

3. A peptide having anti-HIV activity, said peptide consisting of an amino acid chain represented by Asn-Phe-Pro-Leu-Ile-Ile-Lys-Asn-Leu-Lys-Ile-Glu-Asp-Ser-Asp-Thr-Tyr-Ile-Ser-Glu-Val-Glu-Asp-Gln-Lys-Glu-Glu.

4. A peptide having anti-HIV activity, said peptide consisting of an amino acid chain represented by Asn-Phe-Pro-Leu-Ile-Ile-Lys-Asn-Leu-Lys-Ile-Glu-Asp-Ser-Asp-Thr-Tyr-Ile-$Cys^{Acm}$-Glu-Val-Glu-Asp-Gln-Lys-Glu-Glu wherein Acm represents an acetoamidomethyl group.

5. A peptide having anti-HIV activity, said peptide consisting of an amino acid chain represented by Asn-Phe-Pro-Leu-Ile-Ile-Lys-Asn-Leu-Lys-Ile-Glu-Asp-Ser-Asp-Thr-Bzl-Glu-Val-Glu-Asp-Gln-Lys-Tyr-Ile-Cys-Glu-Glu wherein Bzl represents a benzyl group.

* * * * *

UNITED STATES PATENT AND TRADEMARK OFFICE
CERTIFICATE OF CORRECTION

PATENT NO. : 5,043,422

DATED : August 27, 1991

INVENTOR(S) : Kohji Ohki, Kita-Ku, Kazuyoshi Ikuta, Kazutaka Ohmura and Shiro Kato It is certified that error appears in the above-identified patent and that said Letters Patent is hereby corrected as shown below:

Abstract, line 4, as reads "Cys-Glu-Val-Glu-Asp-Gln-Lys-Glu-" should be corrected to read -- <u>Cys</u>-Glu-Val-Glu-Asp-Gln-Lys-Glu-Glu --

On column 2, line 40, as reads "Asp-Ser-Asp-Thr-Tyr-Ile-Cys-Glu-Val-Glu-Asp-" should be corrected to read -- Asp-Ser-Asp-Thr-Tyr-Ile-<u>Cys</u>-Glu-Val-Glu-Asp- --

On column 2, line 48, as reads "Asp-Ser-Asp-Thr-Tyr-Ile-Phe-Glu-Val-Glu-Asp-" should be corrected to read -- Asp-Ser-Asp-Thr-Tyr-Ile-<u>Phe</u>-Glu-Val-Glu-Asp- --

On column 2, line 55, as reads "Asp-Ser-Asp-Thr-Tyr-Ile-Ser-Glu-Val-Glu-Asp-" should be corrected to read -- Asp-Ser-Thr-Tyr-Ile-<u>Ser</u>-Glu-Val-Glu-Asp- --

On column 2, line 62, as reads "Asp-Ser-Asp-Thr-Tyr-Ile-CysAcm-Glu-Val-Glu-" should be corrected to read-- Asp-Ser-Asp-Thr-Tyr-Ile-<u>Cys</u>$^{Acm}$-Glu-Val-Glu- --

On column 3, line 2, as reads "Asp-Ser-Asp-Thr-Tyr-Ile-Cys$^{Bzl}$-Glu-Val-Glu-" should be corrected to read -- Asp-Ser-Asp-Thr-Tyr-Ile-<u>Cys</u>$^{Bzl}$-Glu-Val-Glu- --

On column 3, line 29, as reads "Glu-Asp-Ser-Asp-Thr-Tyr-Ile-Cys-Glu-Val-Glu-" should be corrected to read -- Glu-Asp-Ser-Asp-Thr-Tyr-Ile-<u>Cys</u>-Glu-Val-Glu- --

On column 3, line 32, as reads "Glu-Asp-Ser-Asp-Thr-Tyr-Ile-Phe-Glu-Val-Glu-" should be corrected to read -- Glu-Asp-Ser-Asp-Thr-Tyr-Ile-<u>Phe</u>-Glu-Val-Glu- --

UNITED STATES PATENT AND TRADEMARK OFFICE
CERTIFICATE OF CORRECTION

PATENT NO. : 5,043,422

DATED : August 27, 1991

INVENTOR(S) : Kohji Ohki, Kita-Ku, Kazuyoshi Ikuta, Kazutaka Ohmura and Shiro Kato It is certified that error appears in the above-identified patent and that said Letters Patent is hereby corrected as shown below:

On column 3, line 35, as reads "Glu-Asp-Ser-Asp-Thr-Tyr-Ile-Ser-Glu-Val-Glu- should be corrected to read -- Glu-Asp-Ser-Asp-Thr-Tyr-Ile-$\underline{Ser}$-Glu-Val-Glu- --

On column 3, line 38, as reads "Glu-Asp-Ser-Asp-Thr-Tyr-Ile-$Cys^{Acm}$-Glu-Val-" should be corrected to read -- Glu-Asp-Ser-Asp-Thr-Tyr-Ile-$\underline{Cys}^{Acm}$-Glu-Val- --

On column 3, line 42, as reads "Glu-Asp-Ser-Asp-Thr-Tyr-Ile-$Cys^{Bzl}$-Glu-Val-" should be corrected to read -- Glu-Asp-Ser-Asp-Thr-Tyr-Ile-$\underline{Cys}^{Bzl}$-Glu-Val- --

On column 4, line 49, as reads "Asp-Ser-Asp-Thr-Tyr-Ile-$Cys^{Acm}$-Glu-Val-Glu-Asp-" should be corrected to read -- Asp-Ser-Asp-Thr-Tyr-Ile-$\underline{Cys}^{Acm}$-Glu-Val-Glu-Asp- --

On column 5, line 38, as reads "Asp-Ser-Asp-Thr-Tyr-Ile-$Cys^{Bzl}$-Glu-Val-Glu-" should be corrected to read -- Asp-Ser-Asp-Thr-Tyr-Ile-$\underline{Cys}^{Bzl}$-Glu-Val-Glu- --

On column 6, line 14, as reads "Asp-Ser-Asp-Thr-Tyr-Ile-Cys-Glu-Val-Glu-Asp-" should be corrected to read -- Asp-Ser-Asp-Thr-Tyr-Ile-$\underline{Cys}$-Glu-Val-Glu-Asp- --

On column 6, line 17, as reads "Asp-Ser-Asp-Thr-Tyr-Ile-Phe-Glu-Val-Glu-Asp-" should be corrected to read -- Asp-Ser-Asp-Thr-Tyr-Ile-$\underline{Phe}$-Glu-Val-Glu-Asp- --

UNITED STATES PATENT AND TRADEMARK OFFICE
CERTIFICATE OF CORRECTION

PATENT NO. : 5,043,422

DATED : August 27, 1991

INVENTOR(S) : Kohji Ohki, Kita-Ku, Kazuyoshi Ikuta, Kazutaka Ohmura and Shiro Kato It is certified that error appears in the above-identified patent and that said Letters Patent is hereby corrected as shown below:

On column 6, line 20, as reads "Asp-Ser-Asp-Thr-Tyr-Ile-Ser-Glu-Val-Glu-Asp-" should be corrected to read -- Asp-Ser-Asp-Thr-Tyr-Ile-<u>Ser</u>-Glu-Val-Glu-Asp- --

On column 6, line 49, as reads "gag" should be corrected to read -- <u>gag</u> --

On column 8, line 16, as reads "Asp-Ser-Asp-Thr-Tyr-Ile-Cys-Glu-Val-Glu-Asp-" should be corrected to read -- Asp-Ser-Asp-Thr-Tyr-Ile-<u>Cys</u>-Glu-Val-Glu-Asp- --

On column 8, line 21, as reads "Asp-Ser-Asp-Thr-Tyr-Ile-Phe-Glu-Val-Glu-Asp-" should be corrected to read -- Asp-Ser-Asp-Thr-Tyr-Ile-<u>Phe</u>-Glu-Val-Glu-Asp- --

On column 8, line 26, as reads "Asp-Ser-Asp-Thr-Tyr-Ile-Ser-Glu-Val-Glu-Asp-" should be corrected to read -- Asp-Ser-Asp-Thr-Tyr-Ile-<u>Ser</u>-Glu-Val-Glu-Asp- --

UNITED STATES PATENT AND TRADEMARK OFFICE
CERTIFICATE OF CORRECTION

PATENT NO. : 5,043,422

DATED : August 27, 1991

INVENTOR(S) : Kohji Ohki, Kita-Ku, Kazuyoshi Ikuta, Kazutaka Ohmura and Shiro Kato It is certified that error appears in the above-identified patent and that said Letters Patent is hereby corrected as shown below:

On column 8, line 32, as reads "Asp-Ser-Asp-Thr-Tyr-Ile-Cys$^{Acm}$-Glu-Val-Glu-" should be corrected to read -- Asp-Ser-Asp-Thr-Tyr-Ile-$\underline{Cys}^{Acm}$-Glu-Val-Glu- --

On column 8, lines 37 and 38, as reads "Asp-Ser-Asp-Thr-Bzl-Glu-Val-Glu-Asp-Gln-Lys-Tyr-Ile-Cys" should be corrected to read --Asp-Ser-Asp-Thr-Tyr-Ile-$\underline{Cys}^{Bzl}$-Glu-Val-Glu-Asp-Gln-Lys-Glu-Glu--

Signed and Sealed this

First Day of June, 1993

*Attest:*

*Attesting Officer*

MICHAEL K. KIRK

*Acting Commissioner of Patents and Trademarks*